US012799161B2

(12) United States Patent
Kim et al.

(10) Patent No.: US 12,799,161 B2
(45) Date of Patent: Nov. 17, 2026

(54) PENTAPEPTIDE AND USE THEREOF

(71) Applicant: ENSOL BIOSCIENCES INC., Daejeon (KR)

(72) Inventors: Hae Jin Kim, Daejeon (KR); Eun Joung Moon, Daejeon (KR); Cheol Min Lee, Daejeon (KR); Yun Hee Han, Daejeon (KR)

(73) Assignee: ENSOL BIOSCIENCES INC., Daejeon (KR)

( * ) Notice: Subject to any disclaimer, the term of this patent is extended or adjusted under 35 U.S.C. 154(b) by 364 days.

(21) Appl. No.: 18/710,594

(22) PCT Filed: Oct. 28, 2022

(86) PCT No.: PCT/KR2022/016699
§ 371 (c)(1),
(2) Date: May 15, 2024

(87) PCT Pub. No.: WO2023/090686
PCT Pub. Date: May 25, 2023

(65) Prior Publication Data

US 2025/0059232 A1 Feb. 20, 2025

(30) Foreign Application Priority Data

Nov. 17, 2021 (KR) ........................ 10-2021-0158732

(51) Int. Cl.
*C07K 7/06* (2006.01)
*A61K 38/00* (2006.01)
*A61K 45/06* (2006.01)
*A61P 35/00* (2006.01)

(52) U.S. Cl.
CPC ................ *C07K 7/06* (2013.01); *A61K 45/06* (2013.01); *A61P 35/00* (2018.01); *A61K 38/00* (2013.01)

(58) Field of Classification Search
None
See application file for complete search history.

(56) References Cited

U.S. PATENT DOCUMENTS 10,189,875 B2 * 1/2019 Kim ....................... A61K 38/08

FOREIGN PATENT DOCUMENTS

| | | | |
|---|---|---|---|
| JP | 2004513066 | A | 4/2004 |
| JP | 2013517787 | A | 5/2013 |
| JP | 2018520131 | A | 7/2018 |
| KR | 10-2011-0082954 | A | 7/2011 |
| KR | 10-2016-0089523 | A | 7/2016 |
| KR | 10-1644982 | B1 | 8/2016 |
| KR | 102417762 | B1 | 7/2022 |
| WO | 2007133033 | A1 | 11/2007 |
| WO | 2013186934 | A1 | 12/2013 |
| WO | 2014161118 | A1 | 10/2014 |
| WO | 2017014604 | A1 | 1/2017 |

OTHER PUBLICATIONS

Anroop B. Nair et al, "A simple practice guide for dose conversion between animals and human", J Basic Clin Pharma 2016;7:27-31.
Yun, J.-A. et al., 'N-terminal modification of the tetrapeptide Arg-Leu-Tyr-Glu, a vascular endothelial growth factor receptor-2 (VEGFR-2) antagonist, improves antitumor activity by increasing its stability against serum peptidases', Molecular Pharmacology, Dec. 2019, vol. 96, pp. 692-701.
Thundimadathil, J., 'Cancer treatment using peptides: current therapies and future prospects', Journal of Amino Acids, 2012, vol. 2012, Article ID 967347, pp. 1-13.
Camilio, K. A. et al., 'Combining the oncolytic peptide LTX-315 with doxorubicin demonstrates therapeutic potential in a triple-negative breast cancer model', Breast Cancer Research, Jan. 22, 2019, vol. 21, No. 9, pp. 1-12.

* cited by examiner

*Primary Examiner* — Christina Bradley
(74) *Attorney, Agent, or Firm* — NKL LAW; Jae Youn Kim

(57) ABSTRACT

Proposed are a pentapeptide formed by acetylation of the N-terminus of a peptide consisting of an amino acid sequence represented by SEQ ID NO: 1, a pharmaceutically acceptable salt thereof, and uses thereof. The pentapeptide is stable and effective for inhibition of anticancer drug resistance, inhibition of autophagy in tumor cells, enhancement of immunity, activation of immune cells, promotion of anti-tumor immune response, and/or anticancer therapy.

7 Claims, 13 Drawing Sheets

Specification includes a Sequence Listing.

PENTAPEPTIDE AND USE THEREOF

INCORPORATION OF SEQUENCE LISTING

This application contains a sequence listing submitted in Computer Readable Form (CRF). The CFR file contains the sequence listing entitled "PK002176844.xml", which was created on May 14, 2024 and is 1,763 bytes in size. The information in the sequence listing is incorporated herein by reference in its entirety.

TECHNICAL FIELD

The present disclosure relates to pentapeptides and more particularly to improved pentapeptides and their use.

BACKGROUND ART

Research is being conducted on techniques for treating diseases such as cancer with peptides (see International Patent Application Publication No. WO2017/014604 A1 etc.). The inventors became aware of the need for improvements that had not been paid attention, in the course of research on such peptides.

DOCUMENTS OF RELATED ART

Patent Document (Patent Document 1) International Patent Application Publication No. WO 2017/014604 A1, Jan. 26, 2017, Specification

DISCLOSURE OF INVENTION

Technical Problem

One objective to be accomplished by the present disclosure is to provide an improved pentapeptide.

In addition, another objective to be accomplished by the present disclosure is to provide a novel use of the improved pentapeptide.

The effects, features, and objectives of the present disclosure are not limited to the ones mentioned above, and other effects, features, and objectives not mentioned above can be clearly understood by those skilled in the art from the following description.

Solution to Problem

The inventors have recognized the need for improvement in terms of stability for a peptide consisting of the amino acid sequence of SEQ ID NO: 1 (QLHLD) and thus have conducted study on the subject, resulting in the completion of the invention which is not only superior in terms of stability but surprisingly has previously unanticipated applicability.

The present disclosure provides a pentapeptide formed by acetylation of the N-terminus of a peptide consisting of an amino acid sequence (QLHLD) of SEQ ID NO: 1, or a pharmaceutically acceptable salt thereof.

In the amino acid sequence, Q indicates Glutamine (Gln), L indicates Leucine (Leu), H indicates Histidine (His), and D indicates Aspartate (Asp).

The amino acids present in a peptide include L-amino acids, D-amino acids, and DL-amino acids. The peptide of the invention includes all of these amino acids.

Such peptides include variants, including variants that maintain the key activity of the peptides but are partially altered in the peptide structure by natural or artificial variation.

Examples of the pharmaceutically acceptable salt may include hydrochlorides, sulfates, phosphates, acetates, trifluoroacetates, citrates, tartrates, succinates, lactates, maleates, fumarates, oxalates, methanesulfonates, paratoluenesulfonates, sodium salts, potassium salts, magnesium salts, calcium salts, etc.

The disclosure also provides medicinal uses of the pentapeptide according to the present disclosure or pharmaceutically acceptable salts thereof, and preferably the uses may include suppression of anticancer drug resistance, autophagy inhibition in tumor cells, immune enhancement, immune cell activation, anti-tumor immune response promotion, and/or anticancer. The anticancer uses refer to uses for cancer treatment or prevention. The treatment refers to amelioration of symptoms and the like, and the prevention refers to suppression of development to disease from a pre-disease phase.

The cancer may be a metastatic cancer.

The cancer may be one or more types of cancer selected from breast cancer, prostate cancer, lymphoma, and lung cancer.

The anticancer may be achieved by one or more activities selected from inhibition of resistance to other anticancer drugs, adjuvant to anticancer action of other anticancer drugs, suppression of autophagy in tumor cells, enhancement of immunity, activation of immune cells, promotion of anti-tumor immune response, promotion of tumor cell death, or inhibition of tumor cell proliferation.

The present disclosure provides a pharmaceutical composition for inhibiting anticancer drug resistance, the composition containing the pentapeptide according to the present disclosure or a pharmaceutically acceptable salt thereof as an active ingredient.

The anticancer drug resistance includes a reduction in anticancer drug sensitivity.

The anticancer drug may be any other anticancer agents other than the active ingredient.

The anticancer drug may be a chemotherapeutic agent or an immunotherapeutic agent.

The inhibition of anticancer drug resistance may include inhibition of resistance of an anticancer drug against cancer.

The inhibition of anticancer drug resistance may be achieved by inhibition of autophagy activity in tumor cells or activation of immune cells.

The present disclosure provides a pharmaceutical composition for inhibiting autophagy in tumor cells, the composition containing the pentapeptide according to the present disclosure or a pharmaceutically acceptable salt thereof as an active ingredient.

The pharmaceutical composition may be an autophagy inhibiting agent that inhibits the autophagy activity of cancer cells.

Such autophagy inhibition includes cytoprotective autophagy inhibition.

The inhibition of autophagy may be achieved by inhibition of LC3II protein expression.

The active ingredient may inhibit activated autophagy in cancer cells, thereby inhibiting cancer progression.

When an anticancer drug is administered, autophagy, which is an intracellular digestive process, is activated in tumor cells, and cell organelles damaged by the anticancer drug and degradation products resulting from the process are reused as metabolites of tumor cells due to the activated autophagy. In this case, apoptosis is prevented, and proliferation of tumor cells is promoted. That is, the tumor cells become resistant to the anticancer drug. Therefore, the anticancer drug resistance can be inhibited by the autophagy inhibition of the active ingredient.

The present disclosure provides a pharmaceutical composition for enhancing immunity, the composition containing the pentapeptide according to the present disclosure or a pharmaceutically acceptable salt thereof as an active ingredient.

The immune enhancement may be achieved by activating immune cells in tumors.

The present disclosure provides a pharmaceutical composition for activating immune cells, the composition containing the pentapeptide according to the present disclosure or a pharmaceutically acceptable salt thereof as an active ingredient.

The immune cell may be a natural killer cell or a cytotoxic T cell.

The pharmaceutical composition may be an immune cell activator.

The pharmaceutical composition may be a natural killer cell activator.

The immune cell activation allows for promotion of expression of cell killing factors in tumor cells, promotion of lysis mediated by immune cells (for example, natural killer cells) in tumor cells, apoptosis of tumor cells, and/or extinction of tumors.

The present disclosure provides a pharmaceutical composition for promoting an anti-tumor immune response, the composition containing the pentapeptide according to the present disclosure or a pharmaceutically acceptable salt thereof as an active ingredient.

The present disclosure provides an anticancer pharmaceutical composition containing the pentapeptide according to the present disclosure or a pharmaceutically acceptable salt thereof as an active ingredient.

Additionally, the present disclosure provides a pharmaceutical composition for use in treatment or prevention of cancer, containing the pentapeptide according to the present disclosure or a pharmaceutically acceptable salt thereof as an active ingredient.

The active ingredient may be used in a manner of being co-administered with a third anticancer drug.

The third anticancer drug may be an anticancer chemotherapeutic agent or an anticancer immunotherapeutic agent.

The anticancer chemotherapeutic agent may be one or more agents selected from paclitaxel and doxorubicin.

The anticancer immunotherapy agent may be an immune checkpoint inhibitor.

The immune checkpoint inhibitor can be one or more materials selected from anti-PD-L1 and anti-PD-1.

The active ingredient and the third anticancer agent may be administered concurrently or sequentially.

The active ingredient may be administered 24 hours after administration of the third anticancer agent.

The active ingredient may be administered within 48±12 hours after administration of the third anticancer agent.

The active ingredient may be administered at a dosage of 0.8 to 2000 mg/kg.

The active ingredient may be administered 1 to 7 times per week.

The active ingredient can be administered by injection.

The third anticancer agent may be administered at a dosage of 2 to 20 mg/kg.

The pharmaceutical composition may be an adjuvant assisting in anticancer action of a third anticancer agent.

The assisting may be an action of inhibiting resistance to or side effects of the third anticancer agent or an action of promoting anticancer action of the third anticancer agent.

The pharmaceutical composition may be a pharmaceutical composition for inhibiting autophagy caused by a third anticancer agent or for enhancing the immune activity of immune cells.

The immune activity enhancement may refer to enhancement of granzyme expression of immune cells by the active ingredient.

The pharmaceutical composition may further include a pharmaceutically acceptable excipient. That is, the pharmaceutical composition may include the pentapeptide according to the present disclosure or a pharmaceutically acceptable salt thereof and the excipient.

The pentapeptide according to the present disclosure may be prepared by acetylation of the N-terminus of the peptide represented by SEQ ID NO: 1. First, the peptide represented by SEQ ID NO: 1 can be prepared through forming peptide bonds. For example, peptides can be prepared by solution-phase synthesis or solid-phase synthesis. Examples of methods for forming peptide bonds include an acyl azide method, an acyl halide method, an acylimidazole method, a carbodiimide method, a phosphonium method, an anhydride method, a mixed anhydride method, an oxidation-reduction method, and the use of Woodward's reagent K, etc. Before a condensation reaction starts, carboxyl groups, amino groups, etc. that are not involved in the reaction may be protected, and carboxyl groups, etc. that are involved in the condensation reaction may be activated by an existing method known in the art. Examples of protective groups for protecting carboxyl groups include ester-forming groups such as methyl, t-butyl, aryl, pentafluorophenyl, benzyl, para-methoxybenzyl, or methoxyethoxymethyl. Examples of protective groups for protecting amino groups include tritylcarbonyl, aryloxycarbonyl, cyclohexyloxycarbonyl, trichloroethyloxycarbonyl, benzyloxycarbonyl, t-butoxycarbonyl, and/or 9-fluorenylmethyloxycarbonyl. Examples of active forms of carboxyl groups include mixed anhydrides, azides, acylchlorides, and active esters [esters with alcohols (for example, pentachlorophenol, 2,4-dinitrophenol, cyanomethylalcohol, p-nitrophenol, N-hydroxy-5-norbornene-2,3-dicarboxylimide, N-hydroxysuccinimide, N-hydroxyoxyphthalimide, or 1-hydroxybenzotriazole)], etc. As a solvent that can be used for the condensation reaction to form peptide bonds, benzene, toluene, hexane, acetone, nitromethane, cyclohexane, ether, chloroform, dichloromethane, ethylacetate, N,N-dimethylformamide, dimethylsulfoxide, pyridine, dioxane, tetrahydrofuran, water, methanol, ethanol, etc. may be used solely or in a mixed form. A reaction temperature may be in the range of about −70° C. to 100° C., which is generally used for the reaction and more preferably in the range of −30° C. to 30° C. The reaction for removing a protective group for protecting peptides depends on the type of the protective group used. The reaction may use acid compounds, base compounds, transition metals, etc. that can dislodge the protective group without affecting peptide bonds. The protective groups may be removed by acid treatment, for example, treatment with hydrogen chloride, hydrogen bromide, hydrogen fluoride, acetic acid, methanesulfonic acid, trifluoromethane sulfonic acid, trifluoroacetic acid, trimethylchlorosilane, or mixtures thereof. When performing the acid treatment for the deprotection reaction, anisole, phenol, thioanisole, etc. may be added as adjuvants to facilitate the reaction. The protective groups may be removed using base treatment, for example, treatment with ammonia, diethylamine, hydrazine, morpholine, N-methylpyrrolidine, piperidine, sodium carbonate, or a mixture of these bases. In addition, the protective groups may be removed by transition metal treatment, for example, treatment with zinc, mercury, palladium/hydrogen, etc.

On the other hand, an N-terminal acyl substituent of the peptide may be formed by a known method using an active acyl derivative. Specifically, an acetylation reaction reagent for acetylating the N-terminus of a peptide represented by SEQ ID NO: 1 may be used. Examples of the acetylation reaction reagent include acetic anhydrides, acylhalides (for example acetylchloride, acetylbromide, acetyliodide), and the like. Alternatively, an acetyl group can be introduced to the N-terminus of the peptide by direct condensation with acetic acid.

In addition, the peptide may be purified by a conventional peptide purification method, such as extraction, layer separation, solid precipitation, recrystallization, or column chromatography.

For parental administration, a dose of the pentapeptide according to the present disclosure or a pharmaceutically acceptable salt thereof may vary depending on the subject or condition being treated. For example, the dose may be in a range of 0.8 to 2000 mg/kg. In such ranges, the dose may vary from species to species taking the peptide or salt thereof. For example, the dose may be in a range of 10 to 100 mg/kg for mice (body weight 20 g), a range of 500 to 2000 mg/kg for rats (body weight 250 g), a range of 40 to 400 mg/kg for dogs (body weight 7 kg), and a range of 0.8 to 324.3 mg/kg, more specifically, a range of 2 to 8 mg/kg for humans (body weight 60 kg). When administered at such doses, the peptide or salt thereof may be more safely effective. The numbers described above may refer to the amount taken at one time. The peptide or salt thereof may be administered 1 to 7 times a week, depending on the subject. For oral administration, the dose is 2 to 5 times the parenteral dose. The pentapeptide according to the present disclosure is mainly administered by parenteral methods, for example, topical injection, intravenous or subcutaneous injection, intracerebral or intrathecal administration, nasal administration, or rectal administration. Alternatively, the pentapeptide may be administered orally as needed.

The pentapeptide or composition according to the present disclosure may be formulated with pharmaceutically acceptable excipients to form injections, suppositories, powders, nasal drops, granules, tablets, and the like.

The pharmaceutically acceptable excipients may be applied according to a number of factors well known to those skilled in the art. The factors taken into consideration when deciding the pharmaceutically acceptable excipients include: particular bioactive substances used and their concentration, stability, and intended bioavailability; diseases and conditions to be treated; age, size, and general conditions of subjects to be treated; and routes of administration, such as nasal, buccal, ocular, topical, transdermal, intramuscular administration, and the like. The factors taken into consideration, however, are not limited thereto. In general, pharmaceutically available excipients used for administration of physiologically active substances by administration routes other than the oral administration include D5W (5% glucose in water) and an aqueous solution containing dextrose and physiological salts in a volume ratio of 5% or less. In the case of topical injection into the lesion, various injectable hydrogels may be used to enhance the therapeutic effect and to increase the duration. In addition, the pharmaceutically available excipients may also include additional ingredients that can enhance the stability of active ingredients, including preservatives and antioxidants. The pentapeptide or composition according to the present disclosure can be prepared by any suitable method used in the art to which the present disclosure pertains and may preferably be formulated depending on diseases or ingredients, with reference to the methods disclosed in well-known literatures and the like related to pharmaceutical science.

The pentapeptide according to the present disclosure may be stored as a physiological saline solution or may be lyophilized in ampoules after addition of mannitol or sorbitol thereto. When the pentapeptide is used for administration, the pentapeptide may be dissolved in saline, water for injection, and the like.

The present disclosure also provides a method of inhibiting anticancer drug resistance, a method of inhibiting autophagy in tumor cells, a method of enhancing immunity, a method of activating immune cells, a method of promoting anti-tumor immune response, and/or a method of treating and/or preventing cancer, in which all of these methods involve administration of the pentapeptide or pharmaceutically acceptable salts thereof according to the present disclosure into subjects. The subjects may require the pentapeptide according to the present disclosure or a pharmaceutically acceptable salt thereof. The subjects may include or exclude humans. The subjects may be mammals. The pentapeptide or pharmaceutically acceptable salt thereof administered to the subject may be an effective amount of the pentapeptide or pharmaceutically acceptable salt thereof. The pentapeptide or pharmaceutically acceptable salt thereof and a third anticancer agent may be concurrently or sequentially administered. The subject may be an individual in which anticancer agent resistance is developed.

In addition, the present disclosure provides uses of the pentapeptide according to the present disclosure or a pharmaceutically acceptable salt thereof, in which the uses include the preparation of autophagy inhibitors, immune enhancers, immune cell activators, anti-tumor immune response promoters, and/or anticancer agents.

Unless otherwise indicated, regarding the pentapeptide or pharmaceutically acceptable salts, uses, compositions, and methods of the present disclosure are equally applied unless contradicted by one another.

Advantageous Effects of Invention

The pentapeptide according to the present disclosure is stable and effective for inhibition of anticancer drug resistance, inhibition of autophagy in tumor cells, enhancement of immunity, activation of immune cells, promotion of anti-tumor immune response, and/or anticancer therapy.

MODE FOR THE INVENTION

Figure 1:
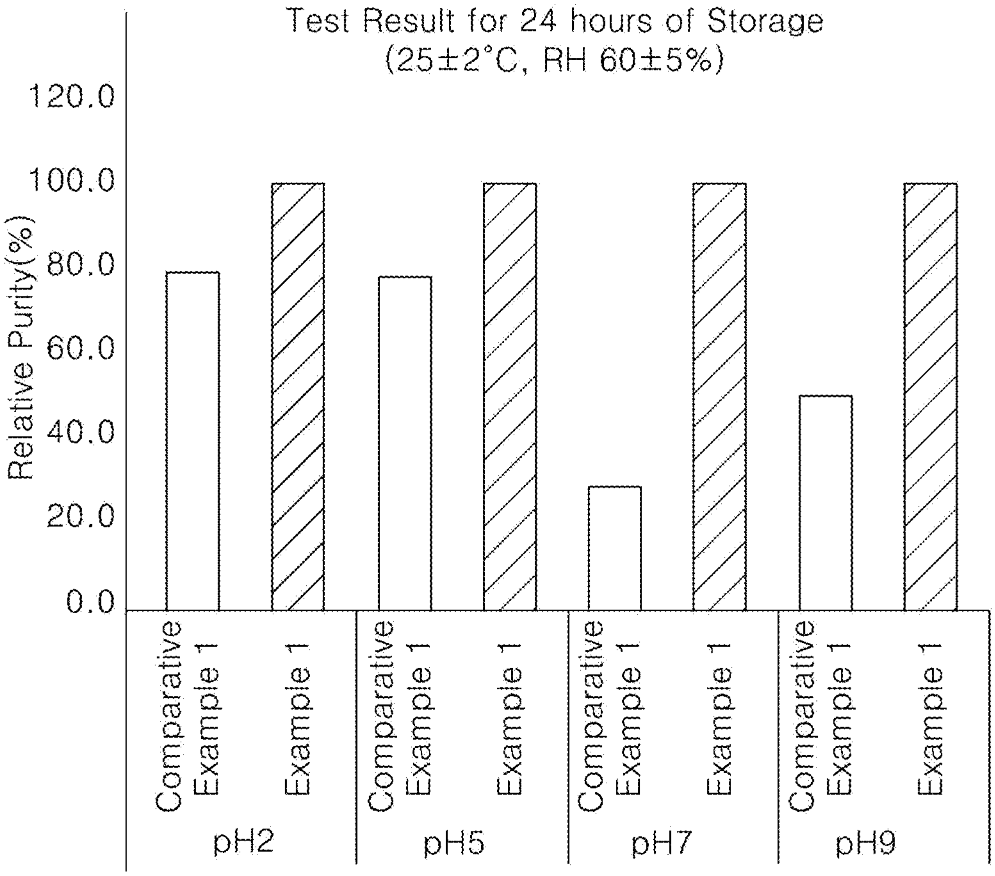
FIG. 1 is a graph illustrating the results of stability tests of Examples and Comparative Examples at a storage temperature of 25° C.

Hereinafter, examples and preparation examples will be described in more detail, but the examples and preparation examples described below are merely illustrative of the present invention and are not intended to limit the present invention thereto.

Hereinafter, reagents and materials used in the examples and the like were commercially available products, and the best products were used. Unless otherwise noted, the reagents and materials used in the examples were products purchased from Sigma-Aldrich.

<Example 1> Preparation of Pentapeptide with N-Terminus Acetylated

Pentapeptides that can be obtained by acetylating the N-terminus of a peptide consisting of an amino acid sequence represented by SEQ ID NO: 1 (QLHLD) were custom-manufactured by Shanghai AmbioPharm, Inc. (in China). Specifically, the pentapeptides were prepared from H-Asp(OtBu)-2-ClTrt solid resin (substitution rate: 0.63 to 0.67 mmol/g), which is a starting material, by a standard florenylmethyloxycarbonyl solid phase peptide synthesis (Fmoc-SPPS) method.

First, a well-dried reactor (hereinafter, conveniently referred to as first reactor) was charged with 12.50 g of the starting material, i.e., H-Asp(OtBu)-2-ClTrt peptide resin, and N,N-dimethylformamide (DMF, 125 ml, 10 mL/g resin) was added thereto. The content in the reactor was stirred for 20 minutes so that the resin was swollen, and then filtered. The filtrate was discarded and the resin was washed twice with N,N-dimethylformamide (DMF, 75 ml, 6 mL/g resin).

Another reactor (hereinafter, conveniently referred to as second reactor) was charged with Fmoc-Leu-OH (1.5 equivalents per 1 equivalent of starting material) and hydroxybenzotriazole (HOBt, 1.5 equivalents per 1 equivalent of starting material), and N,N-dimethylformamide (DMF, 4.5 mL per gram of the starting material) was added thereto for dissolution, followed by addition of diisopropylethylamine (DIPEA, 1.5 equivalents per 1 equivalent of starting material). The reaction solution was cooled to a temperature range of 0° C. to 5° C., and then O-(benzotriazol-1-yl)-N,N,N',N'-tetramethyluronium hexafluorophosphate (HBTU, 1.5 equivalents per 1 equivalent of starting material) was added to the reaction solution so that an amino acid derivative was activated.

Dichloromethane (1.5 mL per 1 g of the starting material) was added to the first reactor containing the peptide resin serving as the starting material, and the activated amino acid derivative solution prepared in the second reactor was slowly introduced into the first reactor. The resulting content in the first reactor was stirred at a reaction solution temperature in a range of 10° C. to 30° C. for 2 hours. The reaction was checked using a ninhydrin (Kaiser) test. After the reaction was completed, the peptide resin was filtered and then washed once with each of the solvents N,N-dimethylformamide (DMF) and methyl t-butyl ether (MTBE). After that, the peptide resin was further washed two times with N,N-dimethylformamide (DMF). (75 ml, 6 mL/g resin)

The following fluorenylmethyloxycarbonyl (Fmoc) deprotection reaction was carried out. In this process, the peptide reaction resin was treated with a 5% piperidine mixed solution (v/v/w/v: 5% piperidine/1.25% DBU/1% HOBt/DMF) twice (75 ml, 6 mL/g resin, filtered after stirring for 10 minutes) for the deprotection reaction, and then filtered. After the filtration, the peptide reaction resin was washed twice with N,N-dimethylformamide (DMF), twice with methyl t-butyl ether (MTBE), and twice with N,N-dimethylformamide (DMF) (6 mL/g resin). The fluorenylmethyloxycarbonyl (Fmoc) deprotection reaction was checked by a ninhydrin (Kaiser) test.

Coupling to #3, #4, #5 amino acid derivatives and the fluorenylmethyloxycarbonyl (Fmoc) deprotection reaction were repeated to synthesize Fmoc-Gln (Trt)1-Leu2-His(Trt) 3-Leu4-Asp (OtBu)5-2-ClTrt peptide resin. That is, a cycle composed of sequential coupling of amino acids to the peptide resin using #3 reaction Fmoc-His(Trt)-OH, #4 reaction Fmoc-Leu-OH, and #5 reaction Fmoc-Gln(Trt)-OH, and the florenylmethyloxycarbonyl (Fmoc) deprotection reaction was repeated for synthesis of the Fmoc-Gln(Trt)1-Leu2-His(Trt) 3-Leu4-Asp(OtBu)5-2-ClTrt peptide resin. However, in the case of the #3 Fmoc-His(Trt)-OH reaction, the coupling reaction was performed from dichloromethane/N, N-dimethylformamide(DCM/DMF) to N, N-hydroxybenzotriazole/N,N'-diisopropylcarbodiimide.

The fluorenylmethyloxycarbonyl (Fmoc) group at the N-terminus of the Fmoc-Gln(Trt)1-Leu2-His(Trt)3-Leu4-Asp(OtBu)5-2-ClTrt peptide resin was removed through addition of a 5% piperidine mixed solvent (v/v/w/v: 5% piperidine/1.25% DBU/1% HOBt/DMF), stirring, filtration, and washing, so that H-Gln(Trt)1-Leu2-His(Trt)3-Leu4-Asp (OtBu)5-2-ClTrt peptide resin, which is a peptide resin from which the fluorenylmethyloxycarbonyl (Fmoc) group is removed, was synthesized.

Next, the N-terminal acetylation reaction of the synthesized peptide resin was performed. Specifically, acetic anhydride (1 equivalent per equivalent of starting material), pyridine (10 equivalents per equivalent of starting material equivalent), and a solution composed of the synthesized peptide resin and dichloromethane/N,N-dimethylformamide (DCM/DMF) solvent (⅓ per gram of resin, v/v, 4 to 6 mL) were added and stirred at room temperature for 2 hours to undergo the acetylation reaction. A ninhydrin (Kaiser) test was used to check whether the acetylation reaction was complete. The Ac—H-Gln(Trt)1-Leu2-His(Trt) 3-Leu4-Asp (OtBu)5-2-ClTrt peptide resin resulting from the completed reaction was washed with solvent N,N-dimethylformamide (DMF) once, with methyl t-butyl ether (MTBE) once, with N,N-dimethylformamide (DMF) three times, and with methyl t-butyl ether (MTBE) three times (6 ml per gram of resin). Next, vacuum drying was performed at 26° C. for about 44.8 hours to obtain 21.42 grams of peptide resin. The yield was 109.5% based on weight gain with respect to the starting material, i.e., H-Asp (OtBu)-2-ClTrt resin.

Another reactor (hereinafter, conveniently referred to as third reactor) was charged with a deprotection mixed solution, i.e., a mixture of trifluoroacetic acid (TFA), triisopropylsilane (Tis), and dichloromethane (DCM) (TFA/Tis/DCM: 55/5/40 v/v/v, 45 ml, 10 mL per 1 g of peptide resin), and the reaction temperature was lowered to be in a range of 0° C. to 5° C. The temperature of the reaction solution was kept below 17° C. (which is highest temperature, preferably falling within a range of 13.8° C. to 14.6° C.) while the peptide resin obtained was slowly added to the cooled solution. The reaction solution was heated to a temperature range of 23° C. to 27° C. and stirred at this elevated temperature for 90 minutes. The reaction solution was filtered through a polytetrafluoroethylene (PTFE) filter, and the resulting solid resin was washed twice with trifluoroacetic acid (TFA) (1.0 mL per gram of peptide resin, two times). The filtrate was collected and vacuum concentrated at or below 30° C. to remove 70%-80% of the solvent. A pre-cooled methyl t-butyl ether (MTBE) solvent (about 10 folds relative to the volume of the evaporation residue) was added to the concentrated residue to produce crude peptide as a solid precipitate. The resulting solid precipitate was stirred at room temperature for 1 hour, filtered, and washed 5 times with cooled methyl t-butyl ether (MTBE) solvent (50% of MTBE for precipitation). The filtered crude peptide was vacuum dried at 24° C. for about 30 hours to synthesize 5.74 g of crude peptide with a deprotection peptide yield of 98.4% and a HPLC purity of 91.3% to 97.5%.

For purification, 5.74 g of the crude peptide was added to 20 ml of purified water, and ammonia water ($NH_3 \cdot H_2O$, 50 mL) was slowly added dropwise thereto to adjust the pH to 9.00±0.10 so that the crude peptide can be dissolved. The solution was filtered through a filter to remove insoluble materials. The filtrate of the crude filtrate was loaded onto a Prep RP-HPLC column packed with C18 reversed phase resin and subjected to purification using a water-and-acetonitrile mixture.

To remove the solvent of the purified fraction, vacuum concentration was performed in a temperature range of 35° C. to 40° C. so that the majority of the acetonitrile (AN) solvent was removed. The pH of the concentrated solution was adjusted to 4.00±0.10 by slowly adding acetic acid (AcOH) dropwise at room temperature while the concentrated solution was stirred. The pH-adjusted solution was stirred at the same temperature for 16 hours to crystallize the desired peptide so that a solid precipitate was obtained. The precipitate resulting from the crystallization was filtered and washed with an acetic acid/water solution (AcOH/$H_2O$, pH 4.0). The washed solid was introduced into 50 ml of purified water to prepare a homogeneous slurry, and the slurry was loaded into a lyophilizer tray for lyophilization. Finally, 2.8 g of acetyl-QLHLD pentapeptide with an HPLC purity of 99.6% was obtained as a white or cream white lyophilized compound. The molecular weight of the synthesized pentapeptide was 666.71.

<Comparative Example 1> Preparation of Peptide

The peptide disclosed in International Patent Application Publication No. WO 2017/014604 A1 was prepared as Comparative Example 1. The peptide QLHLD of Comparative Example 1 was manufactured by AnyGen Co., Ltd. (Republic of Korea) by order. Specifically, the peptide was synthesized by florenylmethyloxycarbonyl (Fmoc) solid phase peptide synthesis. More specifically, the peptide was synthesized by coupling the C-terminus of an amino acid to a solid phase resin using a solid phase resin (Wang Resin; Sigma-Aldrich, substitution rate 0.55 mmol/g).

An amino acid derivative coupling reaction was performed using O-(benzotriazol-1yl)-N,N,N',N'-tetramethyluronium hexafluorophosphate (HBTU) and amino acid derivatives protected by t-butyl and t-butyloxycarbonyl groups. After the completion of the reaction, the cleavage in the resin and the deprotection were performed for 3 hours at room temperature using a solution of trifluoroacetic acid and water mixed in a 95:5 (v/v) ratio. The cleaved solution was filtered using a glass filter and the crude precipitate was crystallized by adding a diethylether solvent to the filtrate. The crude peptide precipitate was filtered and washed repeatedly with diethylether before being vacuum dried. The dried crude peptide was dissolved in a small amount of purified water and purified by C18 column (20×250 mm) reverse-phase high-performance liquid chromatography (RP-HPLC). The HPLC purity of the purified and separated peptide solution was checked, and the filtrate with a targeted purity level was lyophilized to produce the QLHLD peptide. The HPLC purity of the synthesized peptide (Comparative Example 1) was 97.6%, and the molecular weight of the synthesized peptide was 624.67.

<Experimental Example 1> Stability Test

For Example 1 and Comparative Example 1, stability tests according to pH for each temperature were performed.

Storage conditions for each sample were set as shown in Table 1. Liquid state in Table 1 indicates that each peptide is completely dissolved in buffer (1 mg/ml).

TABLE 1

| | Storage status | Storage temperature/humidity | Storage period |
|---|---|---|---|
| Comparative Example 1<br>Example 1 | Liquid state (pH 2, pH 5, pH 7, pH 9) | 25 ± 2° C./60 ± 5%<br>40 ± 2° C./75 ± 5% | 24 hours,<br>130 hours |

Stability tests for each peptide were performed by liquid chromatography purity analysis for each temperature and each pH according to analysis timing (initial, 24 hours, 130 hours). HPLC analysis conditions wet set as shown in Table 2, and as a mobile phase, a 0.1 M sodium dihydrogenphosphate (0.1 M $NaH_2PO_4$) buffer solution and acetonitrile were used. Samples were analyzed by injecting 20 ul of each sample with an auto-sample injector, and the analysis column was Inspire C18 (4.6×250 mm, 5 m, 12 nm) manufactured by Dikma. The analysis temperature was 40° C., and a UV wavelength of 215 nm was used.

TABLE 2

| Gradient | | |
|---|---|---|
| Time (min) | Buffer solution (0.1M $NaH_2PO_4$, %) | Acetonitrile (%) |
| 0.0 | 88 | 12 |
| 30.0 | 68 | 32 |
| 30.5 | 20 | 80 |
| 35.0 | 20 | 80 |
| 35.5 | 88 | 12 |
| 40.0 | 88 | 12 |

Figure 2:
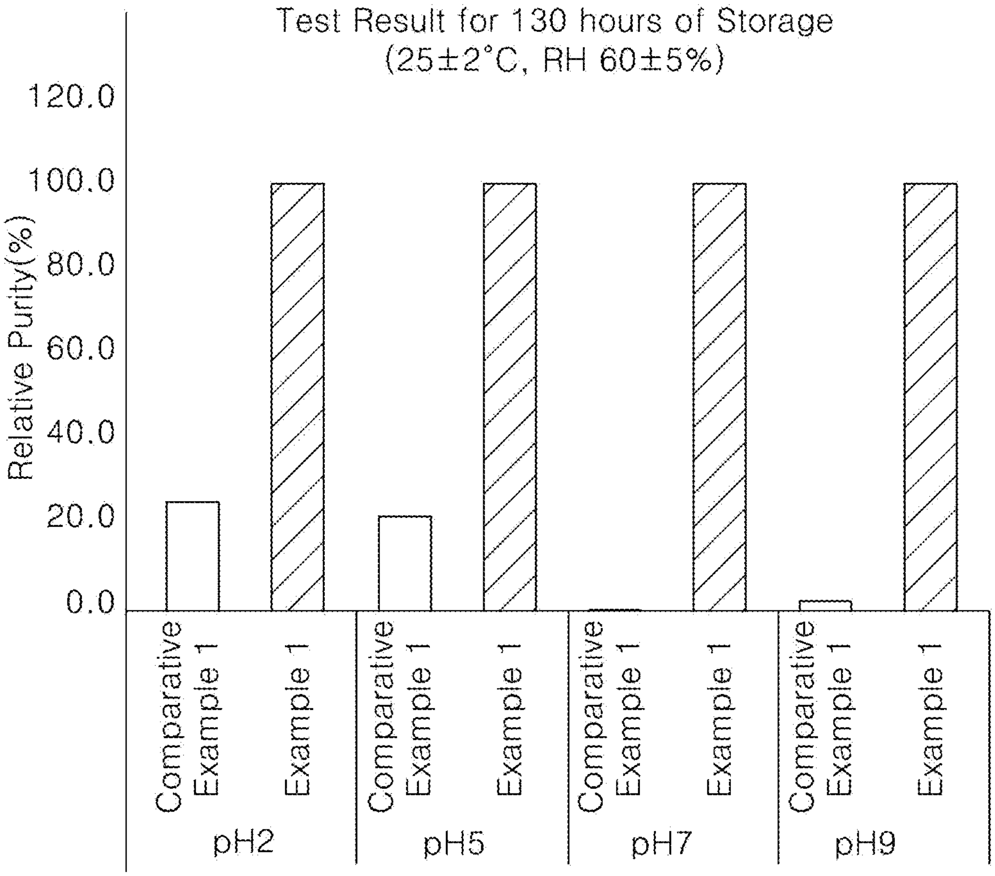
FIG. 2 is a graph illustrating the results of stability tests of Examples and Comparative Examples at a storage temperature of 25° C.
Figure 3:
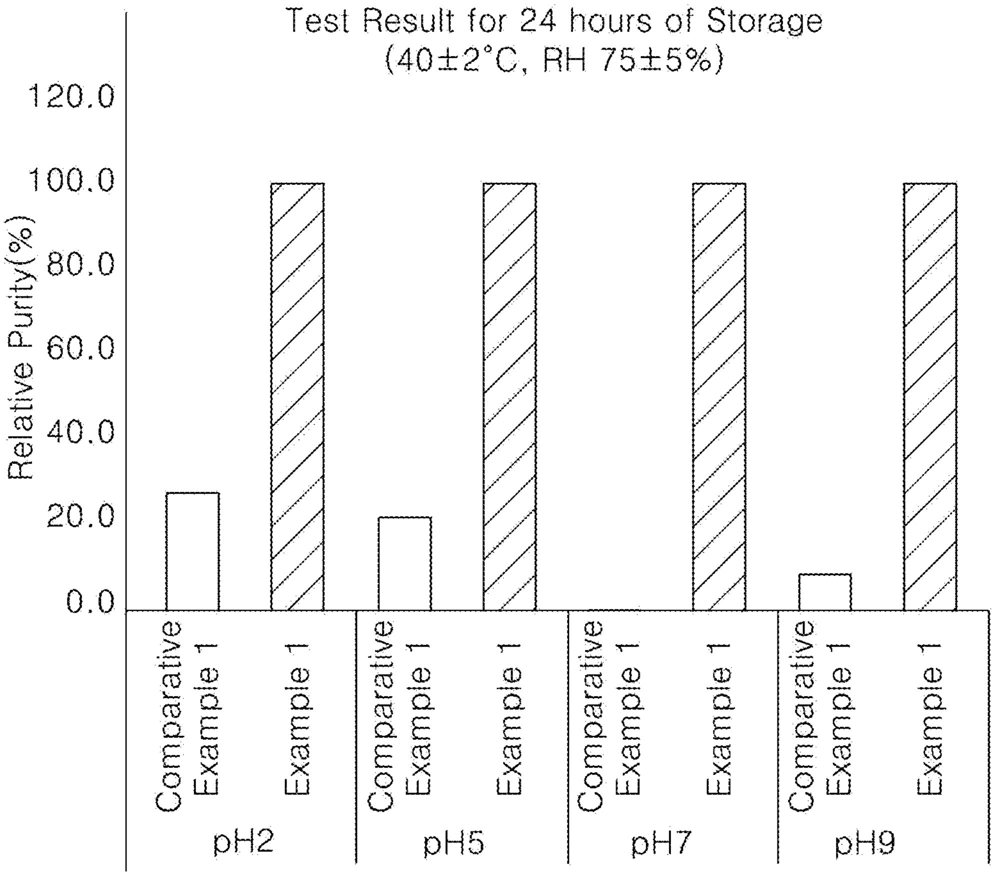
FIG. 3 is a graph illustrating the results of stability tests of Examples and Comparative Examples at a storage temperature of 40° C.
Figure 4:
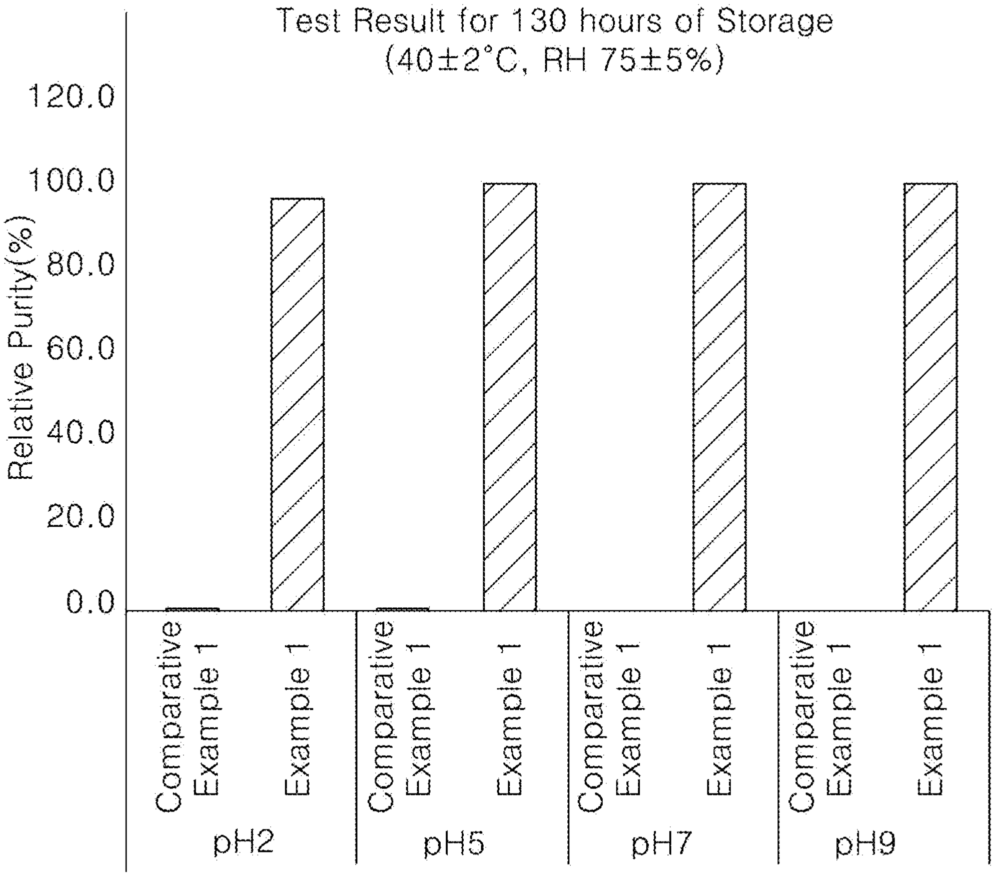
FIG. 4 is a graph illustrating the results of stability tests of Examples and Comparative Examples at a storage temperature of 40° C.

On the basis of the HPLC analysis results, relative purity was calculated for Comparative Example 1 and Example 1 for each storage condition. The relative purity is the percentage of measured purity changing according to the storage period, with the initial purity being set to 100% for each sample. The results are summarized in Table 3 and FIGS. 1 to 4. FIGS. 1 and 2 are graphs showing the results of stability tests for Example and Comparative Example stored at a temperature of 25° C., in which FIG. 1 is a graph of a test result for 24 hours of storage, and FIG. 2 is a graph of a test result for 130 hours of storage. FIGS. 3 and 4 are graphs showing the results of stability tests for Example and Comparative Example stored at 40° C., in which FIG. 3 is a graph of a test result for 24 hours of storage, and FIG. 4 is a graph of a test result for 130 hours of storage. In each graph, the x-axis represents the test group by pH and the y-axis represents the relative purity (0%).

TABLE 3

| Relative purity (%) | | | | |
|---|---|---|---|---|
| | | Storage period (hours) | | |
| pH | Sample | 0 | 24 | 130 |
| Storage conditions: 25 ± 2° C., RH 60 ± 5% | | | | |
| 2 | Comparative Example 1 | 100.0 | 79.0 | 25.0 |
| | Example 1 | 100.0 | 99.7 | 99.9 |
| 5 | Comparative Example 1 | 100.0 | 77.9 | 21.7 |
| | Example 1 | 100.0 | 100.0 | 100.0 |
| 7 | Comparative Example 1 | 100.0 | 28.5 | 0.1 |
| | Example 1 | 100.0 | 100.0 | 100.0 |
| 9 | Comparative Example 1 | 100.0 | 50.2 | 2.4 |
| | Example 1 | 100.0 | 100.0 | 100.0 |
| Storage conditions: 40 ± 2° C., RH 75 ± 5% | | | | |
| 2 | Comparative Example 1 | 100.0 | 27.6 | 0.3 |
| | Example 1 | 100.0 | 99.4 | 95.8 |
| 5 | Comparative Example 1 | 100.0 | 21.8 | 0.1 |
| | Example 1 | 100.0 | 100.0 | 100.0 |
| 7 | Comparative Example 1 | 100.0 | 0.2 | 0.0 |
| | Example 1 | 100.0 | 100.0 | 100.0 |
| 9 | Comparative Example 1 | 100.0 | 8.5 | 0.0 |
| | Example 1 | 100.0 | 99.9 | 99.8 |

As shown in Table 3 and FIGS. 1 to 4, Comparative Example 1 showed that stability varied depending on storage conditions, and in some cases, the samples were not stable. However, Example 1 showed that the samples were extremely stable regardless of storage conditions. In particular, when stored at high temperatures for long periods of time, unlike Comparative Example 1, Example 1 maintained high purity regardless of pH. Thus, it is confirmed that the pentapeptide according to the present disclosure exhibits a remarkable effect that cannot be expected from Comparative Example 1.

<Experimental Example 2> Evaluation of Inhibition of Anticancer Chemotherapeutic Agent Resistance and of Anticancer Effect Using 4T1 cells resistant to paclitaxel, which is one of the chemotherapeutic agents, it was determined whether the peptide of Example 1 exhibited an inhibitory effect for anticancer chemotherapeutic agent resistance. In addition, it was determined whether the peptide of Example 1 exhibited an anticancer effect.

2-1. Evaluation of Inhibitory Effect for Anticancer Drug Resistance

Cell death and autophagy marker changes were determined by the Western blot method, using a syngeneic model implanted with 4T1 cells (American Type Culture Collection (ATCC)), which are mouse triple negative breast cancer tumor cells resistant to paclitaxel. The drug administration was started, when the tumor volume was reached to 70 $mm^3$ after a fat pad of Balb/c mice (6 weeks old, female) was transplanted with 4T1 cells in a concentration of $1\times10^6$ cells/head. For Week 1, paclitaxel 20 mg/kg was administered on Day 1 and Day 2, and the peptide (10, 100 mg/kg) of Example 1 was co-administered on Day 3, Day 5, and Day 7. In addition, the same process was performed for each of Week 2, and Week 3 (n=3). The tumor volumes were measured daily because the tumors grew very quickly. The changes in cleaved PARP, which is a cell death marker, and the changes in LC3II, which is an autophagy marker, in tumors were analyzed after necropsy on the day after the end of the 3-week administration, by a Western blot test.

Figure 5:
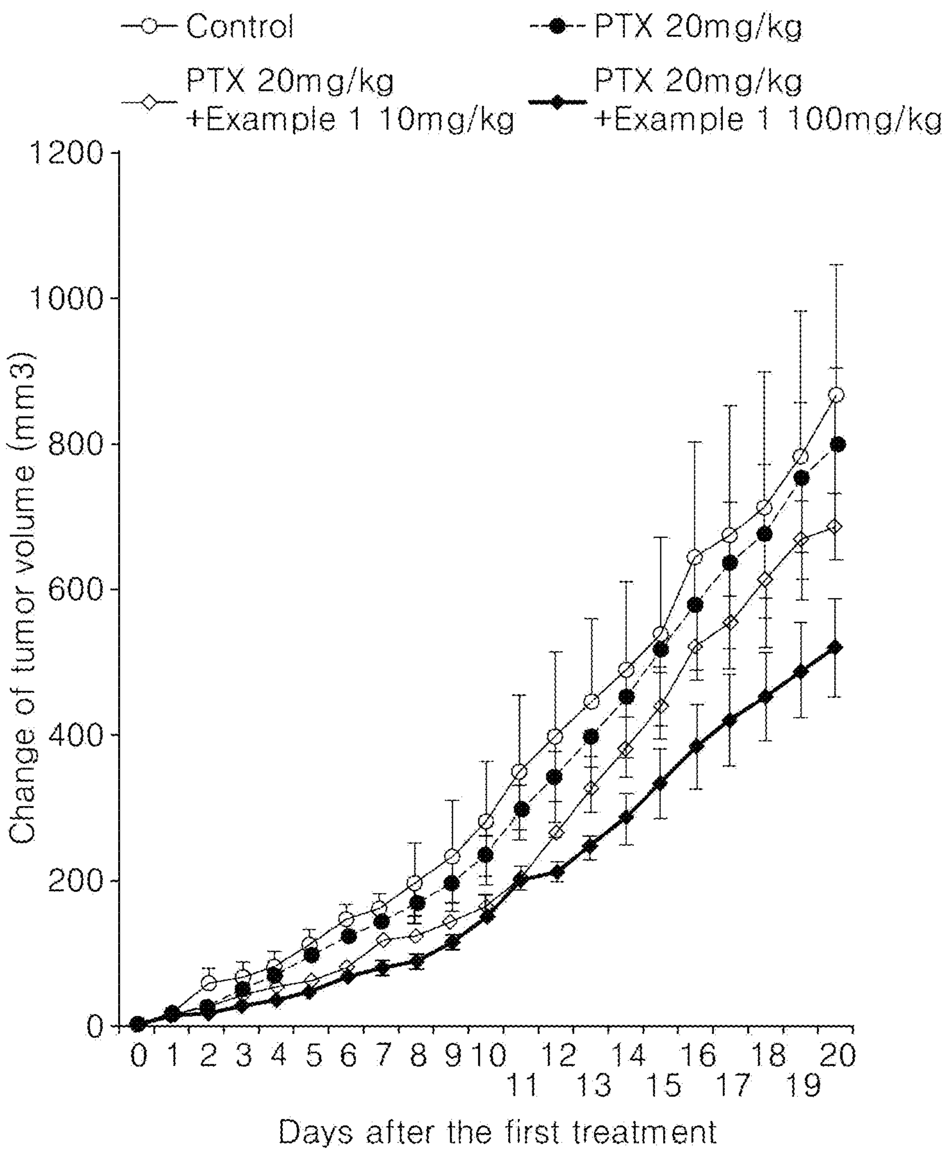
FIG. 5 is a graph illustrating the results of tumor volume measurements according to the number of days after treatment in animal experimentation.

The tumor volume measurement results are shown in FIG. 5. FIG. 5 is a graph illustrating the results of tumor volume measurements according to the number of days after treatment in animal experimentation. In FIG. 5, the x-axis represents the number of days elapsed after treatment and the y-axis represents the tumor volume change ($mm^3$).

As shown in FIG. 5, the group administered with only paclitaxel (PTX) exhibited an insignificant reduction in tumor volume compared to the control group. The group co-administered with paclitaxel and 10 mg/kg of the peptide of Example 1 exhibited a 20% reduction in tumor volume compared to the group administered with only paclitaxel, and the group co-administered with paclitaxel and 100 mg/kg of the peptide of Example 1 exhibited a 40% reduction in tumor volume compared to the group administered with only paclitaxel.

Figure 6:
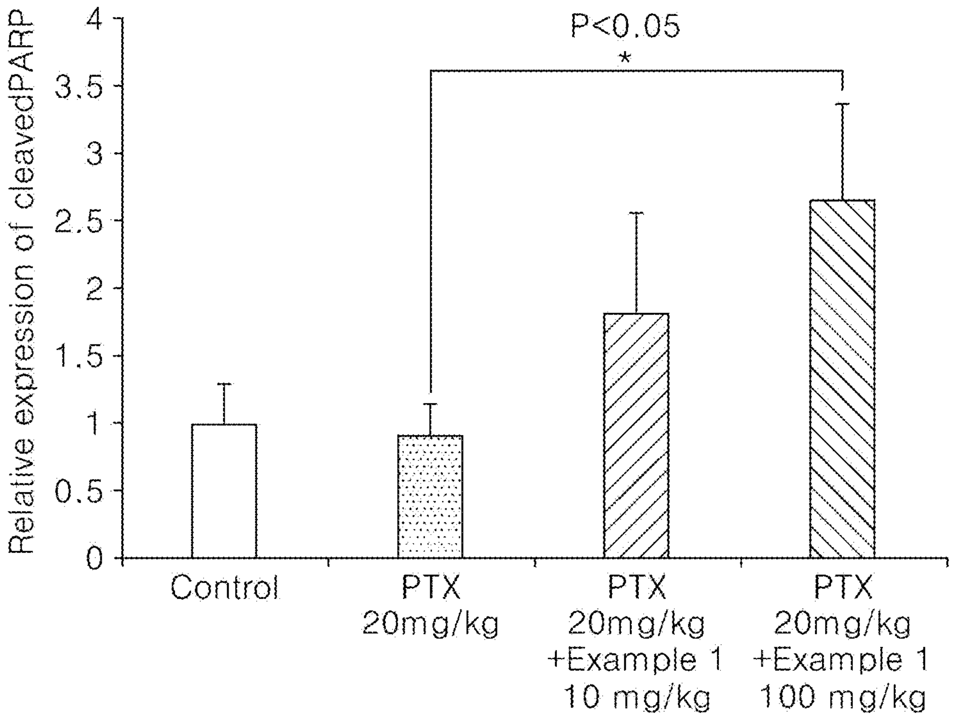
FIG. 6 is a graph illustrating the changes in expression of cleaved PARP, which is a cell death marker, for each treatment group in animal experimentation.
Figure 7:
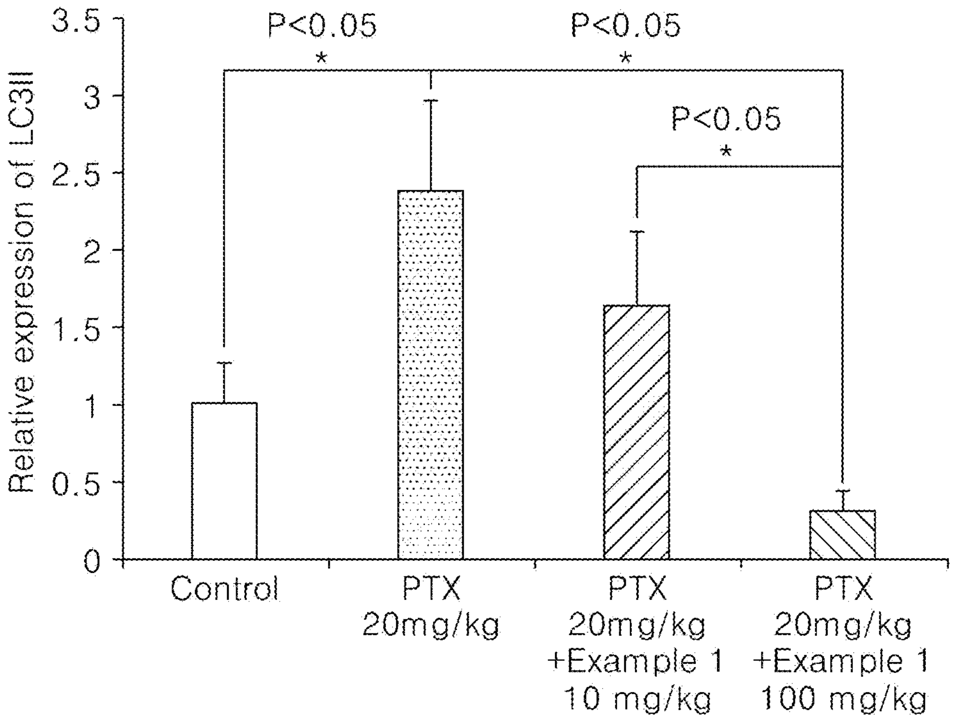
FIG. 7 is a graph illustrating the changes in expression of LC3II, which is an autophagy marker, for each treatment group in animal experimentation.

In addition, the changes in cleaved PARP, which is a cell death marker, are shown in FIG. 6, and the changes in LC3II, which is an autophagy marker, are shown in FIG. 7. FIG. 6 is a graph showing the changes in expression of cleaved PARP, which is a cell death marker, for each treatment group in animal experimentation, and FIG. 7 is a graph showing the changes in expression of LC3II, which is an autophagy marker, for each treatment group in animal experimentation.

As shown in FIG. 6, when the cleaved PARP expression levels are compared, the levels in the groups co-administered with 10 mg/kg of the peptide of Example 1 and 100 mg/kg of the peptide of Example 1 exhibited a 2-fold increase and a 3-fold increase, respectively compared to that in the group administered with only paclitaxel. The level in the group co-administered with 100 mg/kg of the peptide of Example 1 and paclitaxel exhibited a statistical significance ($p<0.05$). In addition, as shown in FIG. 7, when the LC3II expression levels were compared, the level in the group administered with only paclitaxel exhibited a 2.4-fold increase compared to that in the control group, and the levels in the groups co-administered with 10 mg/kg of the peptide of Example 1 and the group co-administered with 100 mg/kg of the peptide of Example 1 exhibited a 38% reduction and a 86% reduction, respectively compared to that in the group administered with only paclitaxel. The level in the group co-administered with 100 mg/kg of the peptide of Example 1 showed a statistical significance ($p<0.05$).

From these results, it is seen that upon combination administration of the peptide of Example 1 and an anticancer agent to tumor cells that are resistant to the anticancer agent, resistance to the anticancer agent is suppressed, and autophagy is inhibited. It is also seen that the combination administration of the peptide of Example 1 and the anticancer agent can increase the apoptotic efficacy of the anticancer agent and inhibit tumor growth.

2-2. Evaluation of Anticancer Effect I

The tests described below were conducted to determine whether the combination administration of the peptide of Example 1 and paclitaxel more highly inhibits tumor growth than the case of paclitaxel-only administration. $5\times10^6$ cells/head of the human triple negative breast cancer cell line MDA-MB-231 (American Type Culture Collection (ATCC)) were mixed with Matrigel and PBS (1:1). 100 ul of the mixture was injected into the right third fat pad of 7-week-old female athymic nude mouse. After the transplantation, drug administration started from an average tumor size of 80 $mm^3$. Paclitaxel 20 mg/kg was administered on Day 0 and on Day 1. That is, the paclitaxel 20 mg/kg was administered a total of two times. Then, the peptide of Example 1 was administered in a dose of 100 mg/kg on Day 2, Day 4, and Day 6. That is, the peptide of Example 1 was administered a total of three times. Tumor volumes were measured 3 times a week for 3 weeks after administration of the first dose. Tumor weights were measured by necropsy after the end of the experiment. For each group, ten mice were used.

In the case of the group administered with only paclitaxel, each mouse showed a steady increase in tumor volume after one week of administration, except for two mice in the group. In one mouse, the tumor disappeared on Day 16 (CR=10%). In the case of the group co-administered with paclitaxel and the peptide of Example 1, the tumor volume was reduced or maintained until the end of Week 2 after administration of the first dose. In two mice, the tumor disappeared on Day 14 (CR=20%).

Figure 8:
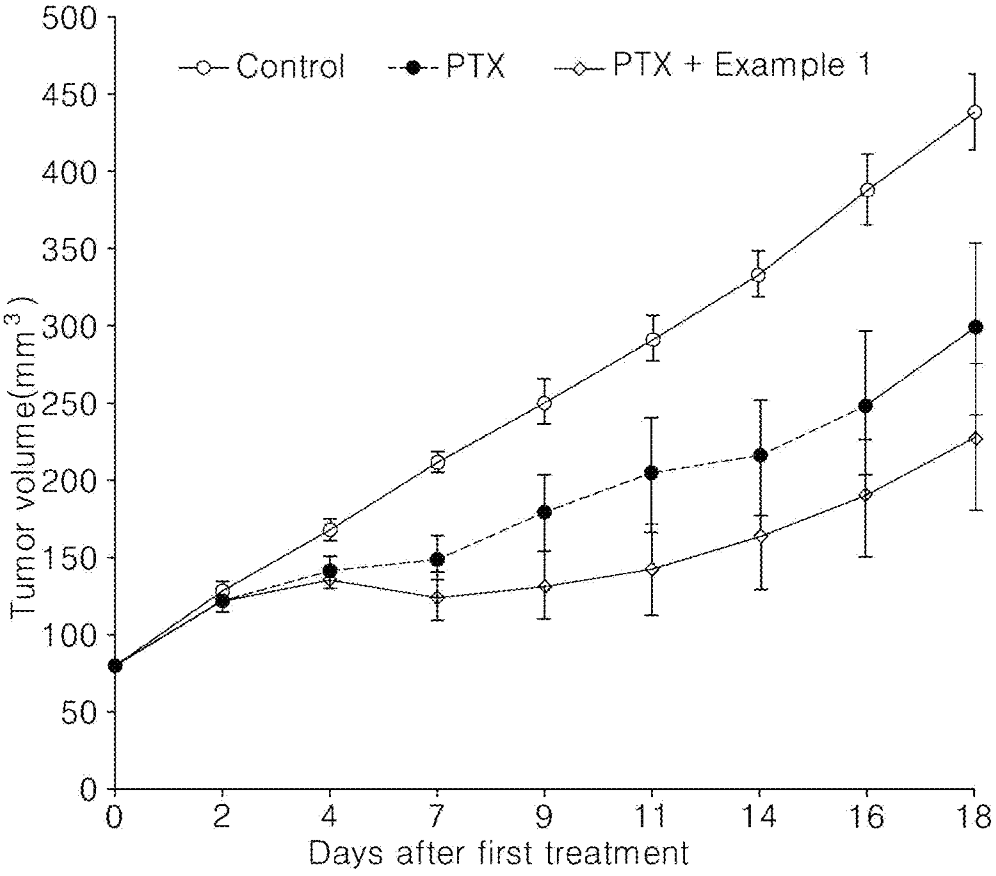
FIG. 8 is a graph illustrating the changes in tumor volume over time after sample administration in animal experimentation.
Figure 9:
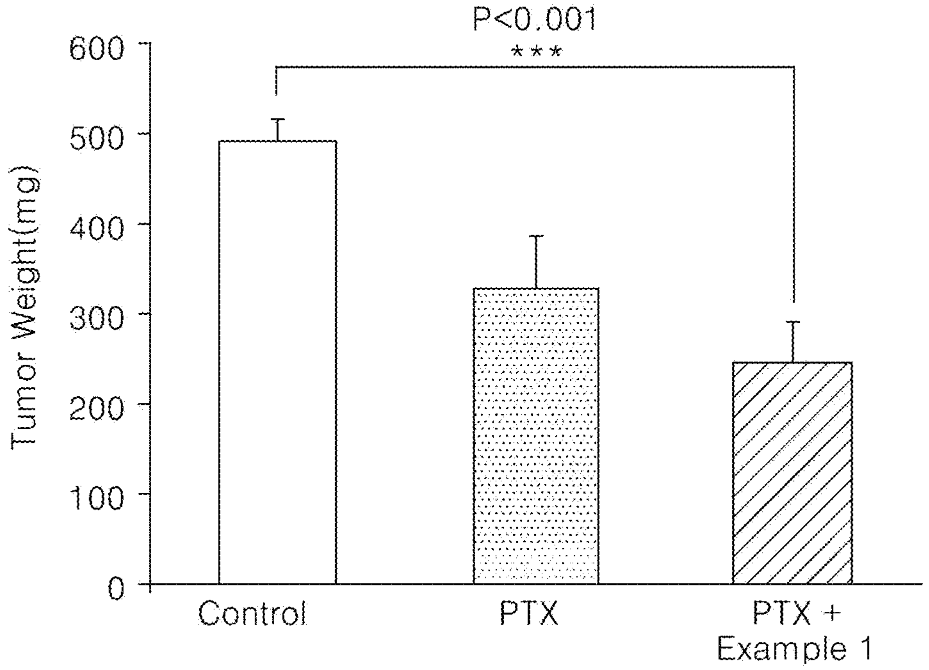
FIG. 9 is a graph illustrating a tumor weight for each test group in animal experimentation.

Tumor volume changes over time for each group are shown in FIG. 8, and tumor weight on the eighteenth day after the administration of the first dose for each group is shown in FIG. 9. FIG. 8 is a graph illustrating the changes in tumor volume over time after sample administration in animal experimentation. In FIG. 8, the x-axis represents the number of days elapsed after the start of administration and the y-axis represents the tumor volume change ($mm^3$). FIG. 9 is a graph illustrating a tumor weight for each test group in animal experimentation. In FIG. 9, the x-axis represents test groups and the y-axis represents tumor weights (mg).

As shown in FIG. 8, the results of the tumor volume measurements on the eighteenth day after the first dose administration showed that the tumor volume in the group administered with only paclitaxel exhibited a 33% reduction compared to that in the control group, and that in the group co-administered with paclitaxel and the peptide of Example 1 exhibited a 48% reduction compared to that in the control group. In addition, as shown in FIG. 9, the results of tumor weight measurements on the eighteenth day after the first dose administration showed that the tumor weight in the group administered with only paclitaxel exhibited a 34.5% reduction compared to that in the control group, and that in the group co-administered with paclitaxel and the peptide of Example 1 exhibited a 51% reduction compared to that in the control group.

In conclusion, the anticancer effect obtained by the combination administration of paclitaxel and the peptide of Example 1 was confirmed, and it can be seen that the efficacy of a single-cycle drug treatment lasted for a maximum of 2 weeks.

2-3. Evaluation of Anticancer Effect II

Figure 10:
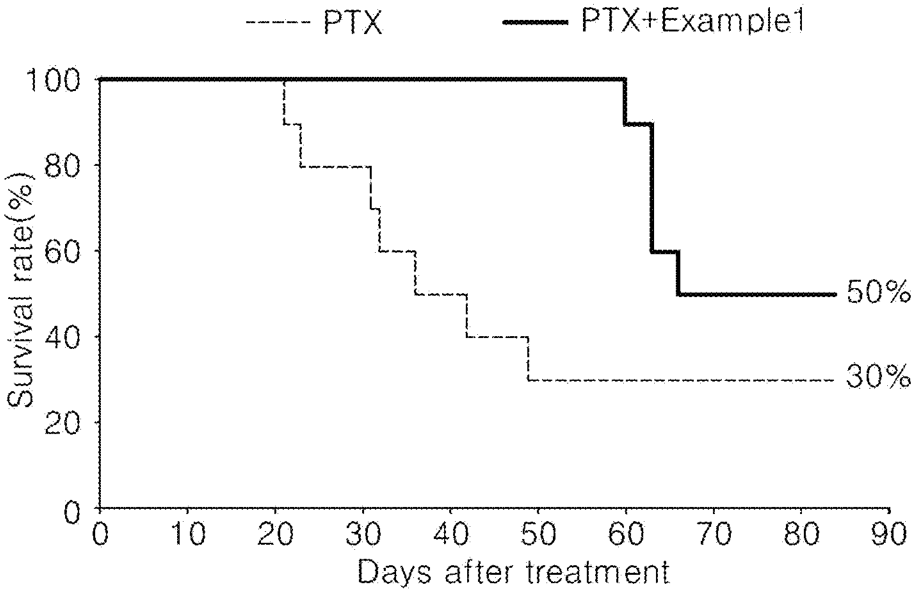
FIG. 10 is a graph illustrating a mouse survival rate over time after sample administration in animal experimentation.

To investigate survival rates of the paclitaxel-only administration group and the group co-administered with paclitaxel and the peptide of Example 1, experiments described below were performed. $5\times10^6$ cells/head of the human triple negative breast cancer cell line MDA-MB-231 were mixed with Matrigel and PBS (1:1). 100 ul of the mixture was injected into the right third fat pad of 7-week-old female BalB/c nude mouse. After the transplantation, drug administration started from an average tumor size of 70 $mm^3$. Paclitaxel 20 mg/kg was administered once weekly, and the peptide 100 mg/kg of Example 1 was administered subcutaneously 3 times weekly at 48-hour intervals, 48 hours after the paclitaxel administration. Each test group was administered for 12 weeks and animal survival was observed daily. The obtained results are shown in FIG. 10. FIG. 10 is a graph illustrating survival rates over time after sample administration in animal experimentation. In FIG. 10, the x-axis represents the elapsed time (days) after administration and the y-axis represents survival rates (%). As shown in FIG. 10, the first deceased mouse occurred in the group administered with only paclitaxel on Day 21 of administration. In the case of the group co-administered with the peptide of Example 1, the first deceased mouse occurred on Day 60 of administration. After the end of the experiment, the group administered with only paclitaxel showed a survival rate of 30% and the group co-administered with paclitaxel and the peptide of Example 1 showed a survival rate of 50%.

From these results, it can be seen that the combination administration of paclitaxel and the peptide of Example 1 increases a survival rate compared to the case of administration of paclitaxel alone. Thus, it can be seen that the peptide of the present disclosure exhibits anticancer effects.

It can also be seen that the case in which the peptide of Example 1 is sequentially administered after the administration of an anticancer agent such as paclitaxel exhibits an effective anticancer effect.

2-4. Evaluation of Anticancer Effect III

Figure 11:
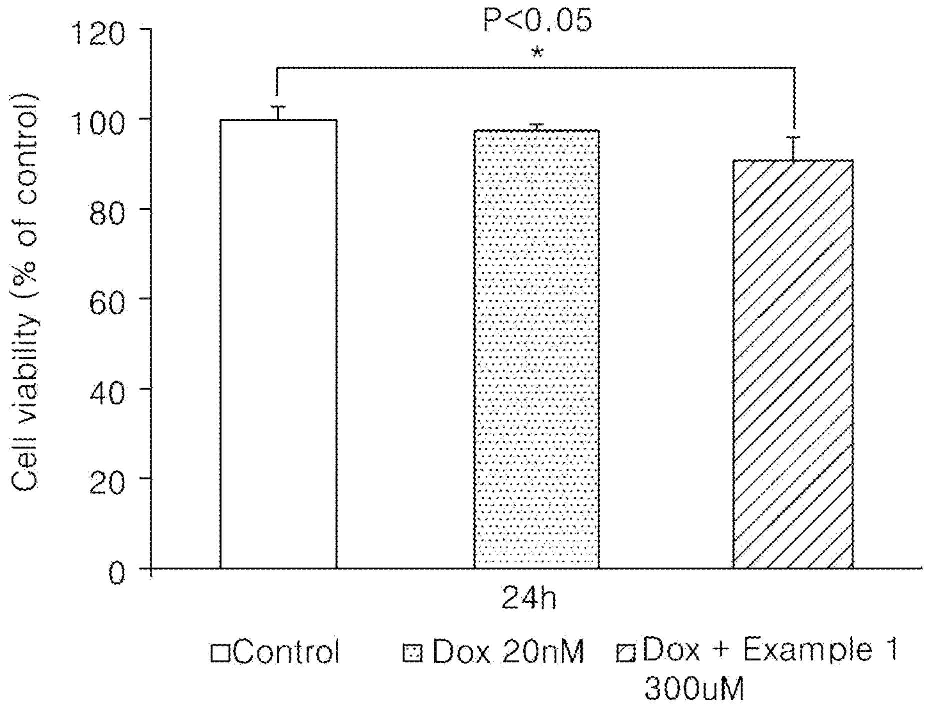
FIG. 11 is a graph illustrating a cancer cell viability for each test group in an anticancer effect evaluation test.

In order to investigate the cell viability by the combined administration of doxorubicin and the peptide of Example 1 compared to the group administered with only doxorubicin, which is an anticancer chemotherapeutic agent, experiments described below were conducted. $8\times10^3$ Cells of the mouse lymphoma cell line EL4 (ATCC) were seeded in 96 wells, which then were treated with doxorubicin 20 nM and peptide 300 uM of Example 1 for each condition. After 24 hours of culturing, the cell viability of the EL4 cells was measured by CCK-8 addition. The obtained results are shown in FIG. 11. FIG. 11 is a graph illustrating the changes in EL4 cell viability over culturing time in an anticancer effect evaluation test. In FIG. 11, the x-axis represents culturing time and the y-axis represents cell viability (%).

As shown in FIG. 11, the group co-treated with the peptide of Example 1 exhibited a significant decrease in cancer cell viability (24 hours, $p<0.05$) compared to the group treated with only doxorubicin (Dox). From these experimental results, it can be seen that the peptide of Example 1 promotes death of tumor cells, indicating anticancer effects.

It can also be seen that the simultaneous administration of an anticancer agent such as doxorubicin and the peptide of Example 1 exhibits an effective anticancer effect.

<Experimental Example 3> Evaluation of Inhibitory Effect for Immune Anticancer Agent Resistance and of Anticancer Effect Using an immune checkpoint inhibitor exhibiting immune anticancer activity, it was determined whether the peptide of Example 1 exhibited an inhibitory effect for immune anticancer agent resistance. In addition, it was determined whether the peptide of Example 1 exhibited an anticancer effect.

Figure 12:
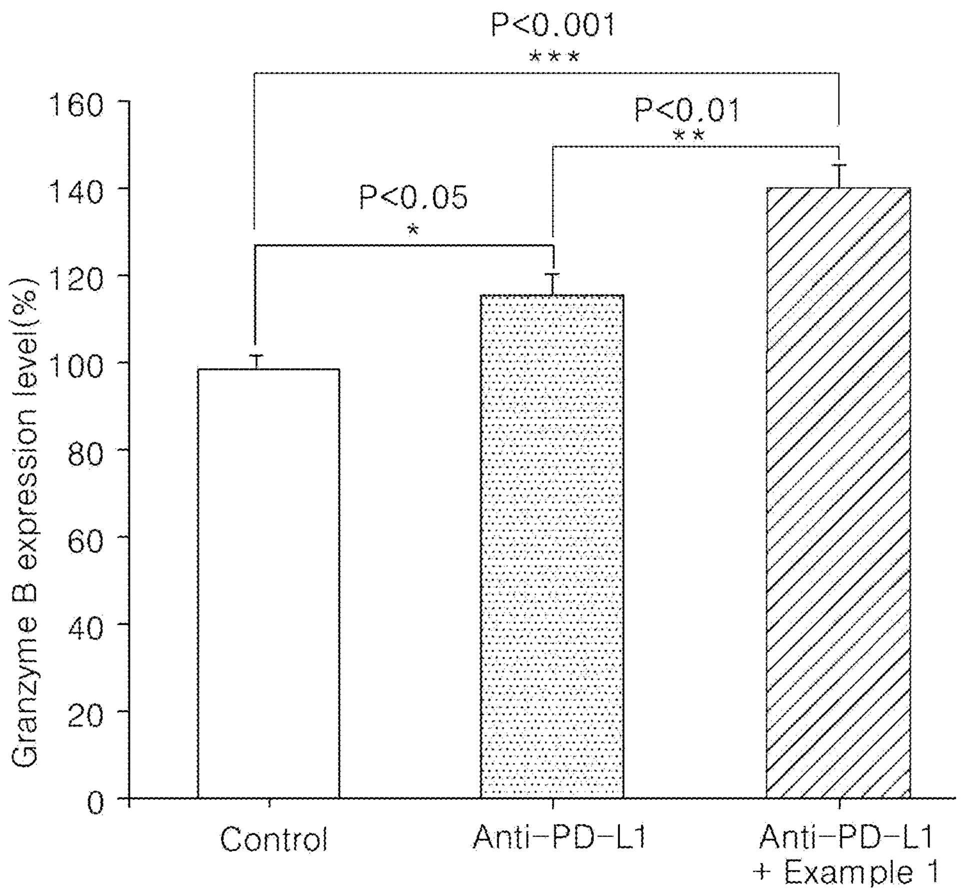
FIG. 12 is a graph illustrating a Granzyme B expression level for each test group in an anticancer effect evaluation test.

3-1. Evaluation of Inhibitory Effect for Immune Anticancer Agent Resistance The experiment described below was performed to identify the tumor suppression mechanism of the combination treatment of the peptide of Example 1 and anti-PD-L1, which is an immune checkpoint inhibitor. First, prostate cancer cell lines PC3 (ATCC) and NK92 (Immunotherapy Research Center, Korea Research Institute of Bioscience and Biotechnology) were co-cultured. $7.8\times10^4$ PC3 cells were seeded in 4-well chambers and stabilized by culturing overnight, and the PC3 cells were treated with 10 μg/ml of the anti-PD-L1 and 300 uM of the peptide of Example 1 for each condition while the same number of NK92 cells were additionally seeded. After 12 hours, the NK92 cells were removed by washing, and only tumor cells were fixed. Next, the expression level of Granzyme B was determined through immuno-fluorescence staining. The Granzyme B expression levels were calculated as proportions relative to the control. The obtained results are shown in FIG. 12. FIG. 12 is a graph showing a Granzyme B expression level for each test group in an anticancer effect evaluation test, in which the x-axis represents the test group and the y-axis represents the Granzyme B expression level (%) relative to the control group.

As shown in FIG. 12, the Granzyme B expression in tumor cells increased significantly in the group co-treated with the peptide of Example 1 compared to the group treated with only the anti-PD-L1. From these results, it is assumed that the peptide of Example 1 activates immune cells such as NK92 cells, increases the expression of Granzyme B, induces a decrease in autophagy in tumor cells, and inhibits the degradation of Granzyme B infiltrating into the tumor cells, thereby increasing intratumoral apoptosis.

Figure 13:
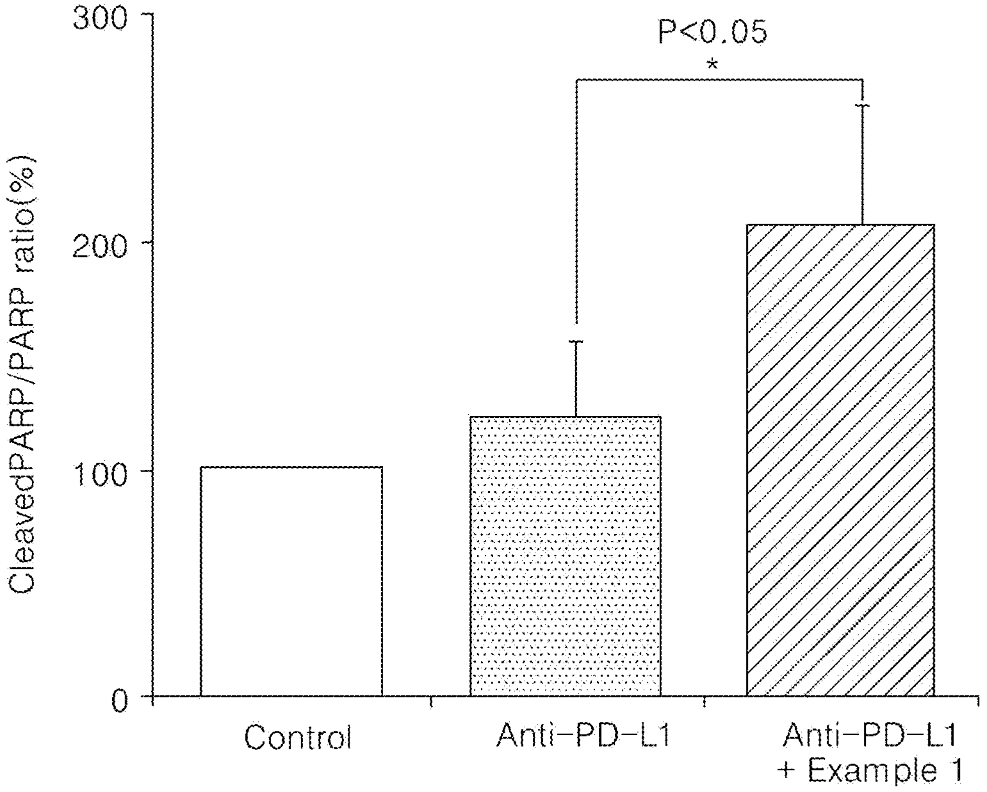
FIG. 13 is a graph illustrating the expression ratio of cleaved PARP to PARP for each test group in an anticancer effect evaluation test.
Figure 14:
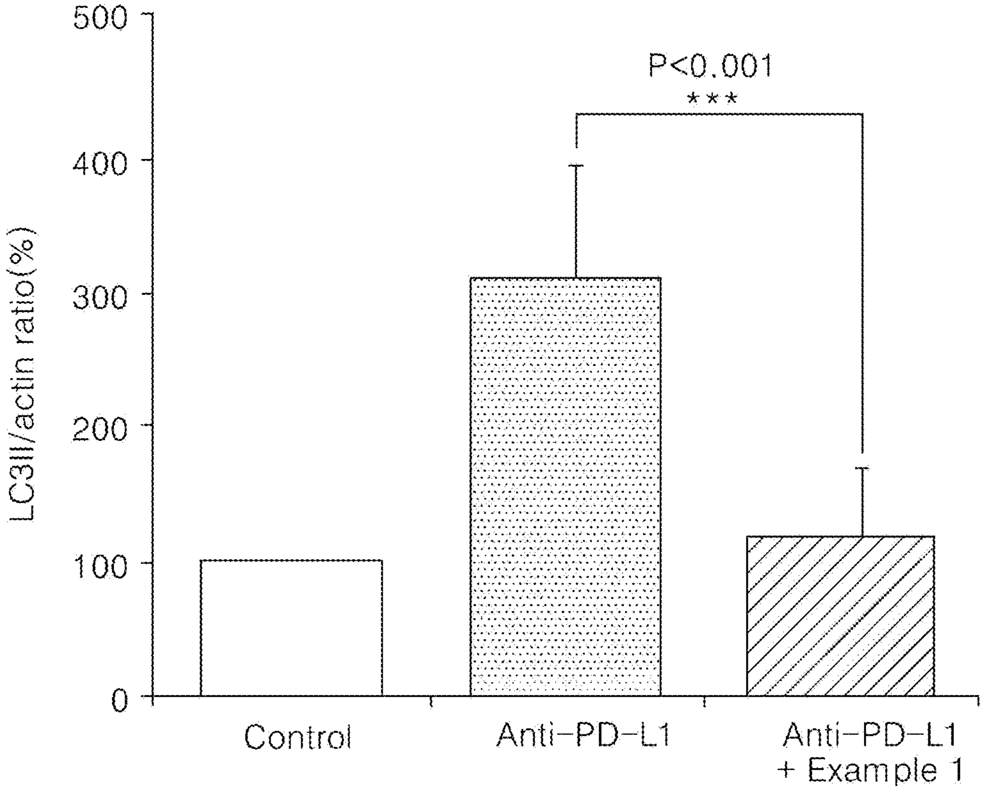
FIG. 14 is a graph illustrating the expression levels of LC3II to actin for each test group in an anticancer effect evaluation test.

In addition, the expression of LC3II, which is an autophagy marker, and the expression of cleaved PARP, which is a cell death marker, were determined by a Western blot test. $1\times10^6$ PC3 cells were seeded in 6 wells and stabilized by culturing overnight, and the PC3 cells were treated with 10 ug/ml of the anti-PD-L1 and 300 uM of the peptide of Example 1 for each condition while the same number of NK92 cells were additionally seeded. After a predetermined period of treatment, the NK92 cells were removed by washing, and proteins were isolated from the tumor cells to determine LC3II (12 h) and PARP (24 h) expression changes. The expression amounts of each marker were calculated as proportions relative to the control. The results are shown in FIGS. 13 to 14. FIG. 13 is a graph showing the amount of cleaved PARP expression compared to PARP for each test group in the anticancer effect evaluation test in which the x-axis represents test groups and the y-axis represents the amount (%) of cleaved PARP expression compared to the PARP. FIG. 14 is a graph showing the amount of LC3II expression compared to actin for each test group in an anticancer effect evaluation test, in which the x-axis represents test groups, and the y-axis represents the amount (%) of LC3II expression compared to actin in the test group.

As shown in FIGS. 13 and 14, the LC3II expression was significantly decreased ($P<0.001$) in the group co-treated with the anti-PD-L1 and the peptide of Example 1 compared to the group treated with only the anti-PD-L1, and the cleaved PARP expression was significantly increased ($P<0.05$). From the results, it is assumed that the Example 1 pentapeptide combination treatment promotes immune cell-mediated lysis (for example, NK-mediated lysis) and inhibits the autophagy of tumor cells, thereby exhibiting inhibitory activity for immunotherapeutic resistance and promoting tumor cell death.

3-2. Evaluation of Anticancer Effect I

Figure 15:
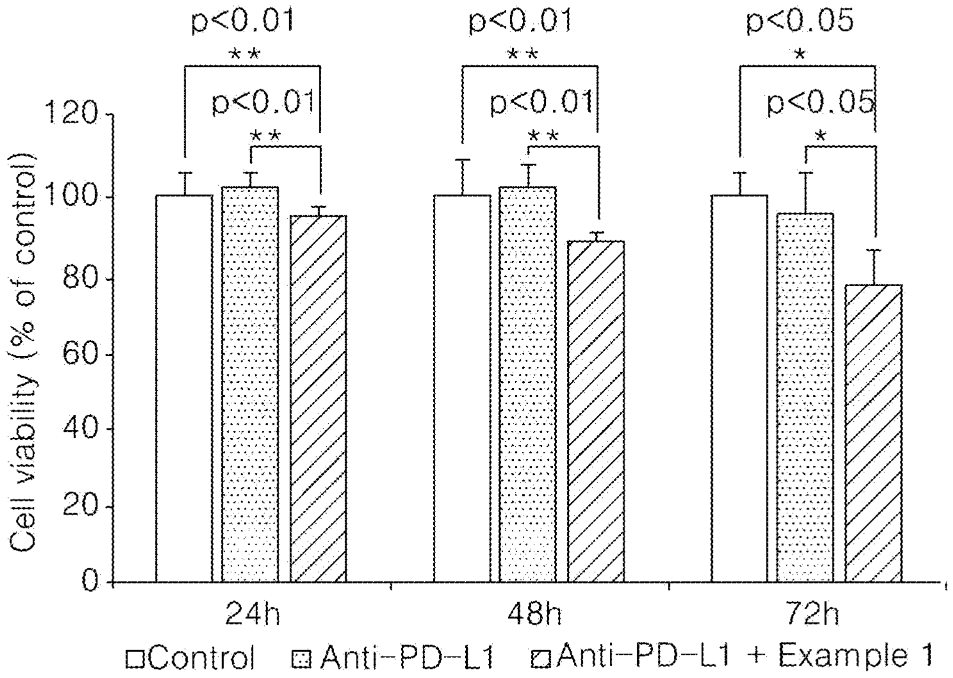
FIG. 15 is a graph illustrating the changes in PC3 cell viability over culturing time for each test group in an anticancer effect evaluation test.
Figure 16:
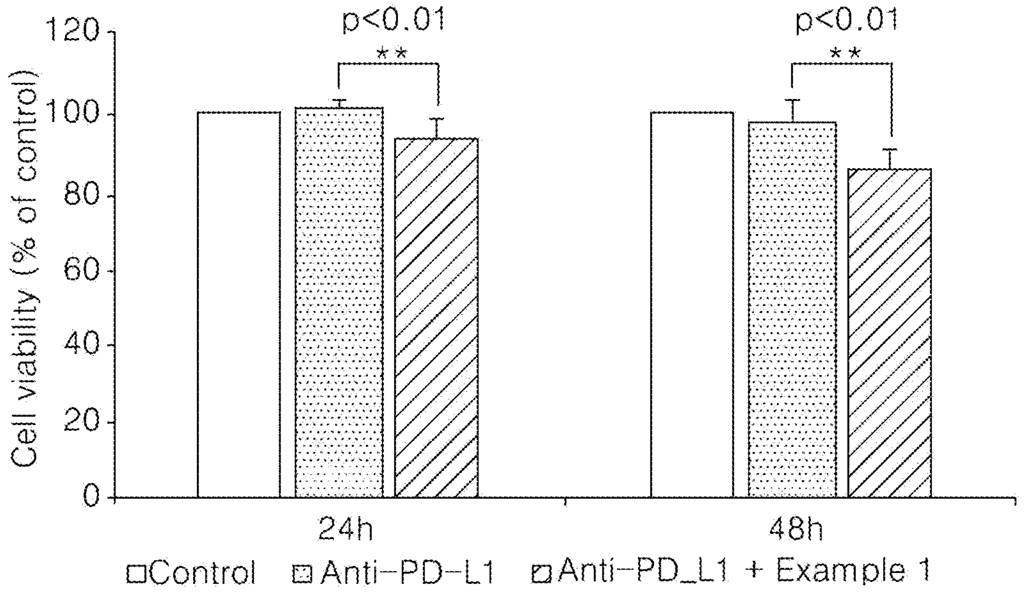
FIG. 16 is a graph illustrating the changes in A549 cell viability over culturing time for each test group in an anticancer effect evaluation test.
Figure 17:
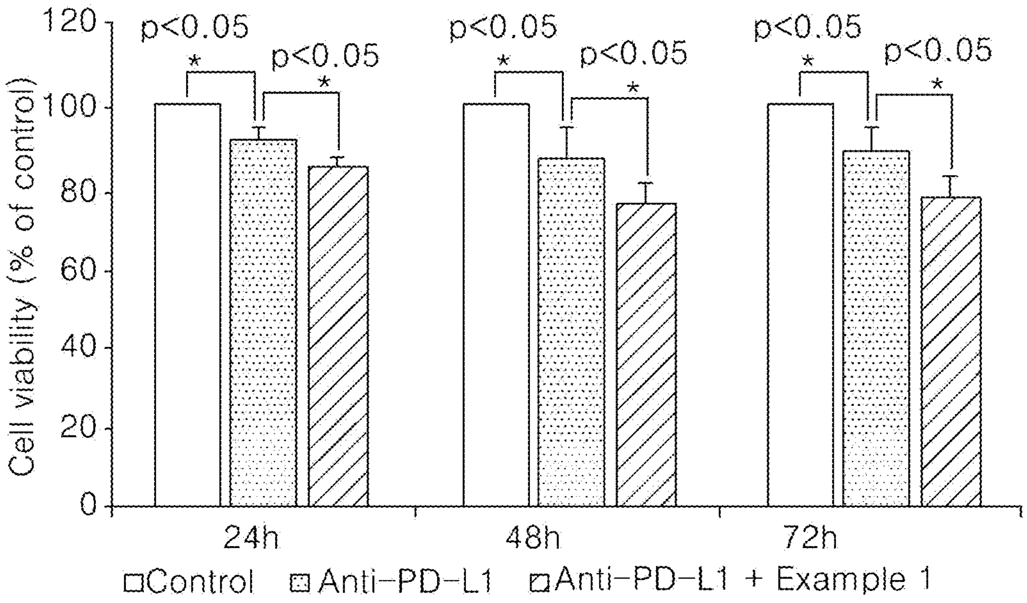
FIG. 17 is a graph illustrating the changes in MDA-MB-231 cell viability over culturing time for each test group in an anticancer effect evaluation test.

The experiment described below was performed to evaluate the tumor cell proliferation inhibitory effect of the combination treatment of the peptide of Example 1 and the anti-PD-L1, which is an immune checkpoint inhibitor. First, $5\times10^3$ cells of a human prostate cancer cell line PC3, $5\times10^3$ cells of a human lung cancer cell line A549 (Korean Cell Line Bank), and $1\times10^4$ cells of a human triple negative breast cancer cell line MDA-MB-231 (ATCC) were seeded in 96 wells and stabilized by culturing overnight. Then, the seeded cells were treated with 10 ug/ml of the anti-PD-L1 and 300 uM of the peptide of Example 1, for each condition while NK92 cells for $5\times10^3$ cells of each of the PC3 cell line and the MDA-MB-231 cell line and $2.5\times10^3$ cells of the A549 cell line were additionally seeded. After 24/48/72 hours of co-culturing (for PC3 and MDA-MB-231) and 24/48 hours of co-culturing (for A549), the NK92 cells were removed by washing, and the cancer cell viability was measured by CCK-8 addition. The results are shown in FIGS. 15 to 17. FIG. 15 is a graph illustrating the changes in PC3 cell viability over culturing time for each test group in an anticancer effect evaluation test. In FIG. 15, the x-axis represents culturing time and the y-axis represents cell viability (%). FIG. 16 is a graph illustrating the changes in A549 cell viability over culturing time for each test group in an anticancer effect evaluation test. In FIG. 16, the x-axis represents culturing time and the y-axis represents cell viability (%). FIG. 17 is a graph illustrating the changes in MDA-MB-231 cell viability over culturing time for each test group in an anticancer effect evaluation test. In FIG. 17, the x-axis represents culturing time and the y-axis represents cell viability (%).

As shown in FIGS. 15 to 17, the group co-treated with the peptide of Example 1 and the anti-PD-L1 exhibited a significant decrease in cancer cell viability as the culturing time increased, compared to the group treated with only anti-PD-L1. From these experimental results, it can be seen that the peptide of Example 1 promotes death of tumor cells, indicating anticancer effects.

3-3. Evaluation of Anticancer Effect II

Figure 18:
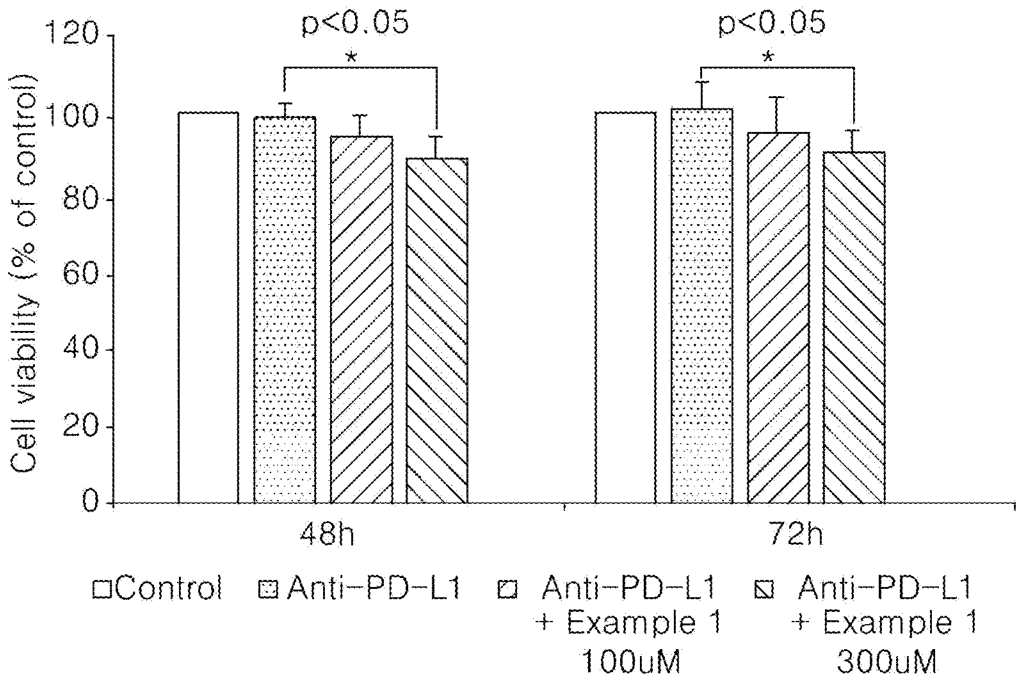
FIG. 18 is a graph illustrating the changes in PC3 cell viability over culturing time for each test group in an anticancer effect evaluation test.

The experiment described below was performed to evaluate the tumor cell proliferation inhibitory effect of the combination treatment of the peptide of Example 1 and anti-PD-1, which is another immune checkpoint inhibitor. First, $5\times10^3$ cells of a human prostate cancer cell line PC3 were seeded in 96 wells and stabilized by culturing overnight. Next, $5\times10^3$ NK92 cells were additionally seeded, and the test cells were treated with 10 μg/ml of the anti-PD-1 and 100 or 300 uM of the peptide of Example 1 for each condition. After 48/72 hours of co-culturing, the NK92 cells were removed by washing, and the cell viability of the PC3 cells was measured by CCK-8 addition. The obtained results are shown in FIG. 18. FIG. 18 is a graph illustrating changes in PC3 cell viability over culturing time for each test group in an anticancer effect evaluation test. In FIG. 18, the x-axis represents culturing time and the y-axis represents cell viability (%).

As shown in FIG. 18, the group co-treated with the peptide of Example 1 and the anti-PD-1 exhibited a significant decrease ($P<0.05$) in cancer cell viability as the culturing time increased, compared to the group treated with only the anti-PD-L1. From these experimental results, it can be seen that the peptide of Example 1 promotes death of tumor cells, indicating anticancer effects.

It can also be seen that the simultaneous administration of an immunotherapeutic agent and the peptide of Example 1 exhibits an effective anticancer effect.

From the results of the experiment, it can be seen that the pentapeptide of Example 1 inhibits resistance of tumors to other anticancer agents (for example, chemotherapeutic agents and immunotherapeutic agents) and exhibits anticancer therapeutic effects by inhibiting autophagy in tumor cells, enhancing immunity, activating immune cells, and promoting anti-tumor immune response.

<Experimental Example 4> Toxicity Test

Ten female and male rats were administered the pentapeptide of Example 1 subcutaneously at doses of 500, 1000, 2000 mg/kg daily for 4 weeks to investigate toxicity, and a safety evaluation test was performed. Specifically, general symptom observation, body weight measurement, feed consumption measurement, ophthalmological examination, and urinary examination were performed. After the end of the observation period, hematology and clinical biochemistry test, organ weight measurement, visual examination at autopsy, and histopathological examination were performed. As a result, no deaths occurred in all test groups, and no adverse findings related to the pentapeptide of Example 1 were observed. Synthesizing the results described above, the no observed adverse effect level (NOEAL) for female and male was determined to be greater than or equal to 2,000 mg/kg/day when the pentapeptide of Example 1 was administered repeatedly subcutaneously to the rats for 4 weeks.

In addition, 3 female and male beagle dogs were used per group to repeatedly subcutaneously administer the pentapeptide of Example 1 at doses of 40, 120, 400 mg/kg for 4 weeks daily. During the test period, general symptom observation, weight and feed intake measurements, ophthalmological examination, electrocardiogram, urinalysis, hematology and clinical biochemistry test, and toxicokinetic examination were performed. In addition, organ weight measurements, visual inspection, and histopathological examination of autopsy subjects were performed. During the test period, no deaths were observed in all female and male animals, including controls. No abnormalities caused by the administration of the pentapeptide of Example 1 were observed in terms of body weight, feed intake, ophthalmic examination, electrocardiogram, urinalysis, hematology and clinical biochemistry test, visual examination at necropsy, and organ weight. The result of the toxicokinetic test showed that the systemic exposure ($AUC_{last}$, $C_{max}$) on Day 1 and Day 28 approximately proportionally increased with increase in the dose, and no pentapeptide accumulation of Example 1 was observed. Thus, the NOAEL (No Observed Adverse Effect Level) of the pentapeptide of Example 1 for female and male beagle dogs under the presented test conditions is determined to be 400 mg/kg/day.

From the results described above, the human equivalent dose (HED) was calculated on the basis of body surface area (J Basic Clin Pharm. 2016 March; 7(2):27-31). The calculation results are shown in Table 4. As shown in Table 4, the human equivalent dose of the pentapeptide of Example 1 was converted on the basis of 0.8 to 8.1 mg/kg for mice, 81 to 324.3 mg/kg for rats, and 21.6 to 216 mg/kg for dogs (beagle dogs). Accordingly, the pentapeptide of Example 1 can be administered at a dose of 0.8 to 324.3 mg/kg to humans.

TABLE 4

| | Minimum Dose (mg/kg) | Maximum Dose (mg/kg) | Human equivalent dose (mg/kg) |
|---|---|---|---|
| Mouse | 10 | 100 | 0.8 to 8.1 |
| Rat | 500 | 2000 | 81 to 324.3 |
| Dog (beagle) | 40 | 400 | 21.6 to 216 |

From the test results described above, it can be seen that when the pentapeptide of Example 1 is administered parenterally (for example, by injection) at a dose of 0.8 to 2000 mg/kg depending on the subject at one time, the effect is safely exhibited. Specifically, the pentapeptide may be administered by one injection at a dose in a range of 10 to 100 mg/kg for mice (body weight 20 g), a range of 500 to 2000 mg/kg for rats (body weight 250 g), a range of 40 to 400 mg/kg for dogs (body weight 7 kg), and a range of 0.8 to 324.3 mg/kg for humans (body weight 60 kg). In this case, the pentapeptide may be administered 1 to 7 times a week depending on the subject. It can also be seen that a third anticancer agent can be administered at an effective dose (for example, 2 to 20 mg/kg) once a week. It can also be seen from the above test results that the pentapeptide of Example 1 is administered concurrently or sequentially with the administration of other anticancer agents to show the effect. Specifically, for humans, the pentapeptide of Example 1 may be administered parenterally (for example, by injection) after paclitaxel administration, or the pentapeptide of Example 1 and an immunotherapy or chemotherapeutic agent other than paclitaxel may be simultaneously administered. For example, upon co-administration of the peptide of Example 1 with paclitaxel for humans, the co-administration may be performed in a manner that paclitaxel is first administered at a dose of 2 to 20 mg/kg and then the pentapeptide of Example 1 is administered parenterally (for example, by injection) at a dose of 0.8 to 324.3 mg/kg, 24 hours (preferably within 48±12 hours) after the administration of the paclitaxel. In this case, each of the paclitaxel and the peptide of Example 1 may be administered once a week. As described above, with the administration of the pentapeptide of Example 1, it is possible to more effectively inhibit drug resistance to other anticancer agents and exhibit anticancer effects.

<Preparation Example 1> Preparation of Injection

The peptide (drug substance) prepared in Example 1 was diluted with a 5-fold amount of water for injection (w/w relative to the weight of the drug substance), 2N NaOH (2 equivalents compared to the drug substance equivalent) was added thereof, and adjusted to the pH 7.0 to be dissolved. The resulting solution was aseptically filtered through a filter (0.22 um), and then lyophilized to prepare a finished drug product (600 mg/vial).

INDUSTRIAL APPLICABILITY

The pentapeptide according to the present disclosure is stable and effective for inhibition of anticancer drug resistance, inhibition of autophagy in tumor cells, enhancement of immunity, activation of immune cells, promotion of anti-tumor immune response, and/or anticancer therapy. Accordingly, the present disclosure has industrial applicability.

```
                          SEQUENCE LISTING


Sequence total quantity: 1
SEQ ID NO: 1             moltype = AA  length = 5
FEATURE                  Location/Qualifiers
source                   1..5
                         mol_type = protein
                         organism = synthetic construct
SEQUENCE: 1
QLHLD                                                           5
```

The invention claimed is:

1. A pentapeptide consisting of the amino acid sequence represented by SEQ ID NO: 1, wherein the N-terminus is acetylated, or a pharmaceutically acceptable salt thereof.

2. A pharmaceutical composition for inhibiting anticancer drug resistance, comprising the pentapeptide of claim 1 or a pharmaceutically acceptable salt thereof as an active ingredient.

3. A pharmaceutical composition for inhibiting autophagy in tumor cells, comprising the pentapeptide of claim 1 or a pharmaceutically acceptable salt thereof as an active ingredient.

4. A pharmaceutical composition for promoting an anti-tumor immune response, comprising the pentapeptide of claim 1 or a pharmaceutically acceptable salt thereof as an active ingredient.

5. A pharmaceutical composition for use in treatment of cancer, comprising the pentapeptide of claim 1 or a pharmaceutically acceptable salt thereof as an active ingredient.

6. The pharmaceutical composition of claim 5, further comprising an anticancer agent.

7. A method of inhibiting anticancer drug resistance, the method comprising administering the pentapeptide of claim 1 or a pharmaceutically acceptable salt thereof to a subject in need thereof.

* * * * *